United States Patent [19]

Druliner et al.

[11] Patent Number: 4,503,257

[45] Date of Patent: Mar. 5, 1985

[54] CYCLOHEXYL HYDROPEROXIDE DECOMPOSITION PROCESS

[75] Inventors: Joe D. Druliner, Newark; Joshua Hermolin, Wilmington, both of Del.

[73] Assignee: E. I. Du Pont de Nemours and Company, Wilmington, Del.

[21] Appl. No.: 495,736

[22] Filed: May 18, 1983

[51] Int. Cl.$^3$ .............................. C07C 45/53
[52] U.S. Cl. .................... 568/342; 568/835
[58] Field of Search ............... 568/342, 835

[56] References Cited

U.S. PATENT DOCUMENTS

| | | | |
|---|---|---|---|
| 2,430,432 | 11/1947 | Marisic | 23/212 |
| 2,609,395 | 9/1952 | Dougherty et al. | 568/357 |
| 2,675,407 | 4/1954 | Gallo et al. | 568/357 |
| 2,851,496 | 9/1958 | Cates et al. | 568/357 |
| 3,093,686 | 6/1963 | Simon et al. | 568/357 |
| 3,404,185 | 10/1968 | Thomas et al. | 568/358 |
| 3,530,185 | 9/1970 | Pugi | 568/357 |
| 3,598,869 | 8/1971 | Volpe et al. | 568/357 |
| 3,855,307 | 12/1974 | Rony et al. | 252/429 R |
| 3,917,708 | 11/1975 | Kuessner et al. | 568/357 |
| 3,923,895 | 12/1975 | Costantini et al. | 568/342 |
| 3,925,316 | 12/1975 | Brunie et al. | 568/342 |
| 3,927,105 | 12/1975 | Brunie et al. | 568/342 |
| 3,941,845 | 3/1976 | Voskuil et al. | 568/342 |
| 3,957,876 | 5/1976 | Rapoport et al. | 568/342 |
| 3,987,100 | 10/1976 | Barnette et al. | 568/342 |
| 3,987,101 | 10/1976 | Wolters et al. | 568/342 |
| 4,042,630 | 8/1977 | Wolters et al. | 568/342 |
| 4,326,084 | 4/1982 | Druliner et al. | 568/342 |
| 4,341,907 | 7/1982 | Zelonka | 568/342 |

Primary Examiner—James H. Reamer
Attorney, Agent, or Firm—Scott G. Hallquist

[57] ABSTRACT

An improvement in a process for decomposing mixtures of cyclohexane and cyclohexyl hydroperoxide is provided. According to the improved process, a mixture comprising cyclohexane and cyclohexyl hydroperoxide is contacted with a catalyst consisting essentially of $Co_3O_4$, $MnO_2$, or $Fe_3O_4$ applied to a suitable solid support, at a temperature from about 80° C. to about 130° C., in the presence of molecular oxygen.

8 Claims, 8 Drawing Figures

CYCLOHEXYL HYDROPEROXIDE
DECOMPOSITION PROCESS

BACKGROUND OF THE INVENTION

This invention relates to an improved catalytic process for decomposing cyclohexyl hydroperoxide in the presence of oxygen to form a mixture containing cyclohexanol and cyclohexanone.

Industrial processes for production of mixtures of cyclohexanol and cyclohexanone from cyclohexane are currently of considerable commercial significance, and are well described in the patent literature. In accordance with typical industrial practice, cyclohexane is oxidized, forming a reaction mixture containing cyclohexyl hydroperoxide (CHHP). The resulting CHHP is decomposed, optionally in the presence of a catalyst, to form a reaction mixture containing cyclohexanol and cyclohexanone. In the industry, such a mixture is known as a K/A (ketone/alcohol) mixture, and can be readily oxidized to produce adipic acid, which is an important reactant in processes for preparing certain condensation polymers, notably polyamides. Due to the large volumes of adipic acid consumed in these and other processes, minor improvements in processes for producing adipic acid and its precursors can provide beneficial cost advantages.

Dougherty, et al., U.S. Pat. No. 2,609,395, disclose a process for oxidation of cycloalkanes to produce cycloalkanols and cycloalkanones, wherein a cycloalkane is reacted with limited quantities of oxygen. The cycloalkane hydroperoxides thereby produced are decomposed by heating in the presence of a cycloalkane, producing cycloalkanols and cycloalkanones.

Gallo, et al., U.S. Pat. No. 2,675,407, disclose optional use of polyvalent metal catalysts in a process for oxidizing cycloalkanes. Specific catalysts disclosed include finely divided metals such as cerium, cobalt, copper, manganese and vanadium, as well as inorganic and organic salts or oxides containing such metals.

Cates, et al., U.S. Pat. No. 2,851,496, disclose a process in which cyclohexane is oxidized with molecular oxygen, optionally in the presence of a catalyst, to provide a mixture containing cyclohexanol, cyclohexanone, and CHHP. According to this process, the resulting CHHP is subsequently decomposed to K and A by heating the mixture in the presence of a bed of solid decomposition catalyst, without adding air or oxygen. Catalysts disclosed by this reference include solid, granular metals or metal oxides deposited upon inert supports. Specific metals disclosed by the Cates patent include iron, cobalt and nickel.

Simon, et al., U.S. Pat. No. 3,093,686, disclose a process for oxidation of cyclohexane to produce mixtures of cyclohexanol and cyclohexanone, wherein oxidation is conducted in the presence of organic acid salts of cobalt, lead, manganese and chromium, which are added to a reactor as solutions in cyclohexane.

Pugi, U.S. Pat. No. 3,530,185, discloses a staged process for oxidizing cyclohexane in which a mixture of gases containing oxygen is introduced to a stream of cyclohexane at a temperature of from 140° C. to 200° C. Optionally, a metal catalyst, e.g., cobalt in the form of a hydrocarbon-soluble compound, is added to the cyclohexane stream.

Constantini, et al., U.S. Pat. No. 3,923,895, disclose a process for decomposing CHHP by heating a solution of CHHP and cyclohexane in the presence of a soluble chromium derivative, which is added to a reactor column as a solution in cyclohexane.

Brunie, et al., U.S. Pat. No. 3,925,316, disclose a method of catalytically decomposing CHHP comprising heating a mixture of CHHP and cyclohexane in the presence of a soluble organic salt or chelated derivative of vanadium, molybdenum, or ruthenium.

Kuessner, et al., U.S. Pat. No. 3,917,708, disclose a process for oxidizing cycloalkanes in the presence of heavy metal salt oxidation catalysts. The anions of the heavy metal salts can be monoalkylphosphate, dialkyl phosphate, monoalkyl sulfate, alkylsulfonic acid, alkylphosphonate or dialkylphosphonate.

Brunie, et al., U.S. Pat. No. 3,927,105, disclose a cascade CHHP decomposition process employing soluble chromium derivatives, including chromium carboxylates and chelated chromium derivatives, which are introduced, in solution, at the base of a reactor column.

Rapoport, et al., U.S. Pat. No. 3,957,876, describe a process for oxidizing cyclohexane in which a cyclohexane-soluble cobalt salt is employed as catalyst. The cobalt salts disclosed include cobalt naphthenate, cobalt octoate, cobalt laurate, cobalt palmitate, cobalt stearate, cobalt linoleate and cobalt acetylacetonate.

Barnette, et al., U.S. Pat. No. 3,987,100, disclose a process for oxidizing cyclohexane in the presence of a binary catalyst system comprising prescribed amounts of cyclohexane-soluble chromium and cobalt salts, wherein CHHP formed during the reaction is decomposed to K and A in the presence of the binary catalyst.

Volpe, et al., U.S. Pat. No. 3,598,869, describe a process wherein cyclohexane is oxidized to form nylon precursors, in the presence of oxygen and a soluble cobalt or chromium catalyst. The step in which cyclohexyl hydroperoxide is decomposed to cyclohexanone and cyclohexanol is not separately discussed.

Wolters, et al., U.S. Pat. No. 3,987,101, discloses a process for producing cycloalkanones and cycloalkanols by decomposing cycloalkyl hydroperoxide in the presence of a solid heterogenous chromium catalyst. However, addition of air or molecular oxygen to a CHHP decomposition mixture is not disclosed or suggested.

Druliner, et al., U.S. Pat. No. 4,326,084, disclose an improved catalytic process for oxidizing cyclohexane to form a reaction mixture containing CHHP, and for subsequently decomposing the resulting CHHP to form a mixture containing K and A. The improvement comprises use of certain transition metal complexes of 1,3-bis(2-pyridylimino)isoindolines as catalysts for cyclohexane oxidation and CHHP decomposition. According to this patent, these catalysts demonstrate longer catalyst life, higher CHHP conversion to K and A, operability at lower temperatures (80°–160° C.), and reduced formation of insoluble metal-containing solids, relative to results obtained with certain cobalt(II) fatty acid salts, e.g., cobalt 2-ethylhexanoate.

SUMMARY OF THE INVENTION

In accordance with the present invention, a process improvement is provided for a process in which cyclohexyl hydroperoxide is decomposed in the presence of oxygen to produce a mixture containing cyclohexanone and cyclohexanol. The improvement comprises decomposing the cyclohexyl hydroperoxide by contacting a reaction mixture containing cyclohexane and from about 0.1 to about 10 percent by weight cyclohexyl hydroperoxide with a catalytic amount of a heterogenous catalyst consisting essentially of $Co_3O_4$, $MnO_2$, or $Fe_3O_4$ applied to a suitable solid support, at a temperature of from about 80° C. to about 130° C., in the presence of molecular oxygen.

DETAILED DESCRIPTION OF THE INVENTION

Figure 1:
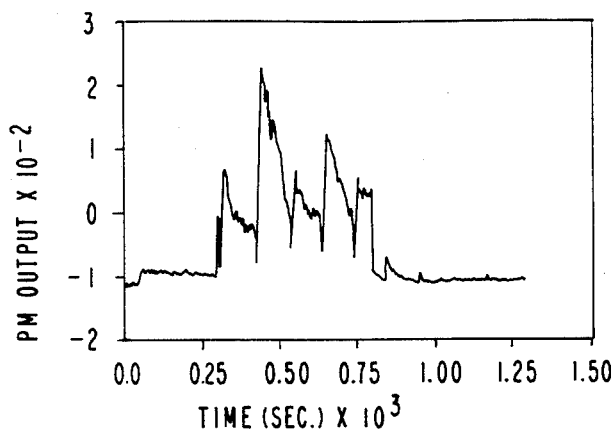
FIGS. 1 through 8 illustrate thermographic and chemiluminescent measurements obtained during experiments in which CHHP was decomposed by the process of the invention, and by other processes known in the art. The FIGS. correspond to Example 6 and Comparative Examples H, I and J, and are discussed in detail below.

The present invention provides an improved process for conducting a cyclohexyl hydroperoxide (CHHP) decomposition step in an industrial process in which cyclohexane is oxidized to form a mixture containing cyclohexanol (A) and cyclohexanone (K). This process involves two steps: first, cyclohexane is oxidized, forming a reaction mixture containing CHHP; second, CHHP is decomposed, forming a mixture containing K and A. As previously mentioned, processes for oxidation of cyclohexane are well described in the literature. Except for specific details described herein, cyclohexane oxidation and CHHP decomposition are to be conducted as described in the literature.

The advantages of the present process, relative to processes employing homogenous metal catalysts, such as metal salts or metal/ligand mixtures, include longer catalyst life, improved yields of useful products, and a more advantageous ratio of K to A in resulting product mixtures. The effect of K/A ratio upon yield of adipic acid in a reaction in which adipic acid precursors are oxidized by nitric acid is described in Barnette, et al., U.S. Pat. No. 3,987,100.

Since CHHP is typically produced industrially as a solution in cyclohexane from catalytic oxidation of cyclohexane, a convenient and preferred solvent for the CHHP decomposition process of the invention is cyclohexane. Such a mixture can be used as received from the first step of the cyclohexane oxidation process or after some of the constituents have been removed by known processes. The concentration of CHHP in the CHHP decomposition mixture can range from about 0.1% to about 10% by weight, preferably from about 0.5% to about 3% by weight.

Suitable reaction temperatures for the process of the invention range from about 80° C. to about 130° C. Temperatures from about 110° C. to about 130° C. are preferred. Reaction pressures can range from about 69 kPa to about 2760 kPa (10–400 psi) gauge pressure, and pressures from about 276 kPa to about 1380 kPa (40–200 psi) are preferred. Reaction time varies in inverse relation to reaction temperature, and typically ranges from about 2 to about 30 minutes.

As noted previously, the heterogenous catalysts of the invention include $Co_3MnO_2$, and $Fe_3O_4$, which are applied to suitable porous solid supports. The ratio of metal oxide to catalyst support can vary from about 1 to about 20 percent by weight, and is preferably about 3 to about 10 percent. Suitable supports include $SiO_2$ (silica), porous glass, $Al_2O_3$ (alumina), $TiO_2$, $ZrO_4$, and activated or inactivated carbon. In the case of porous glass, the ratio of metal oxide to catalyst support can be as low as 0.02 weight percent. Silica and porous glass are preferred supports, and $Co_3O_4$ applied to silica is a preferred catalyst of the invention. The heterogenous catalysts of the invention can be obtained already prepared from manufacturers, or can be prepared from suitable starting materials using methods known in the art.

Silica, alumina, $TiO_2$ or $ZrO_4$ catalyst supports can be amorphous or crystalline, or a mixture of amorphous and crystalline forms. Selection of an optimal average particle size for the catalyst supports will depend upon such process parameters as reactor residence time and desired reactor flow rates. Generally, the average particle size selected will vary from about 1 mm to about 10 mm. To be suitable for use in the process of the invention, catalyst supports should have a minimum surface area of 1 $m^2/g$. Supports having much larger surface areas can also be employed, but inherent brittleness of high-surface area catalysts, and attendant problems in maintaining an acceptable particle size distribution, will establish a practical upper limit upon catalyst surface area.

Porous glass, also known as "thirsty glass", is a leached glass consisting of about 96% $SiO_2$ and 3% $B_2O_3$ (by weight), with traces of other compounds. Porous glass is highly absorbent, having a void space of about 28 volume percent, and a surface area of about 200 $m^2/g$. The preparation and characteristics of porous glass are described in detail by Nordberg, *J. Am. Ceram. Soc.* 27, 299 (1944). Porous glass-can be crushed into a particle size distribution suitable for use in process reactors, and combined with $Co_3O_4$, $MnO_2$ or $Fe_2O_4$ by precipitation, solvent evaporation, or other means, to form a heterogenous catalyst suitable for use in the process of the invention.

The solid catalysts of the invention can be contacted with CHHP decomposition mixtures by formulation into a catalyst bed, which is arranged to provide intimate contact between catalysts and reactants. Alternatively, catalysts can be slurried with reaction mixtures using techniques known in the art. The process of the invention is suitable for batch or for continuous CHHP decomposition processes.

Adding air or gas mixtures containing molecular oxygen to CHHP decomposition mixtures provides higher conversions of process reactants to K and A, since some cyclohexane is oxidized directly to K and A, in addition to K and A formed by CHHP decomposition. This ancillary process is known as "cyclohexane participation", and is described in detail in Druliner, et al., U.S. Pat. No. 4,326,084.

To maximize cyclohexane participation in the CHHP decomposition process and optimize yields of useful products, partial pressures of oxygen in reaction mixtures should be adjusted to provide a molar ratio of molecular oxygen to CHHP of at least 0.5. However, cost and safety considerations, as well as the possibility of formation of insoluble precipitates at relatively high oxygen concentrations, dictate that the maximum partial pressure of oxygen be constrained within reasonable limitations. Preferably, the pressures of air or molecular oxygen, as well as the reactor residence times selected, should be adjusted to provide from about 0.5 to about 4 moles of $O_2$ per mole of CHHP to be decomposed.

Oxygen is generally used as a mixture with an inert gas such as nitrogen or argon. For example, depending on the concentration of oxygen desired, the latter can be supplied as air, as air enriched with added oxygen, or as air diluted with additional nitrogen. Straight air is a convenient and preferred source.

The process of the present invention is further illustrated by the following examples. In the examples, all temperatures are in degrees Celsius and all percentages are by weight unless otherwise indicated.

EXAMPLES

Comparative Examples A–G, and Examples 1–5, which are set forth in Table 2, below, describe a series of experiments in which quantities of CHHP were decomposed in a laboratory pulse reactor to determine effects of variations in catalyst type, temperature, and volume of added air upon CHHP decomposition. The product mixtures were analyzed to determine both the extent of CHHP decomposition and relative amounts of the resulting useful products. Comparative Examples A–F and Examples 1–5 demonstrate CHHP decomposition catalyzed by $Co_3O_4$ applied to a $SiO_2$ support. Comparative Example G illustrates a CHHP decomposition reaction under experimental conditions similar to a conventional plant operation, using a commonly-employed commercial catalyst, Co(II)ethylhexanoate (Co(oct)$_2$).

The 5% $Co_3O_4/SiO_2$ catalyst employed in the Examples was prepared by precipitating a $Co(NO_3)_2.6H_2O$ solution upon a quantity of silica by evaporation of water in a rotary evaporator. The silica granules employed had an average particle diameter of about 3 mm, and a surface area of about 60 m$^2$/g. The resulting composition was calcined by heating to 400° in a stream of air, thereby decomposing the nitrate to $Co_3O_4$ and volatile nitrogen oxides. After cooling, the composition was ground to a fine powder prior to use.

Comparative Examples H, I and J, and Example 6, as illustrated by FIGS. 1–8, provide a semiquantitative comparison, based upon thermographic and chemiluminescent data, of CHHP decomposition reactions conducted with different catalysts and in the presence and absence of added air. Comparative Example H and Example 6 describe experiments using the $Co_3O_4/SiO_2$ catalyst of the invention. The experiments described in Comparative Examples I and J were undertaken using a soluble Co(II) derivative of 1,3-bis(4-ethyl-2-pyridylimino)isoindoline (Co(4EtBPI)$_2$), as disclosed by Druliner, et al., U.S. Pat. No. 4,326,084. The apparatus and procedures employed in these experiments are described below.

Apparatus

The apparatus used for the Comparative Examples and Examples was a stainless-steel pulse reactor having a volume of about 125 ml and usable at internal pressures up to about 2070 kPa (300 psi) gauge pressure. The reactor had a pressure-relief valve to insure that allowable pressure was not exceeded and was equipped with a side-arm with a septum for injection of liquid from a hypodermic syringe. Liquid contents (typically about 25 ml) in the apparatus could be stirred by an external magnetic drive. Heating was provided by partial immersion in a fluidized bed regulated by a proportional heater control. Temperatures were measured with a platinum resistance thermometer having a digital temperature display and analog output.

The reactor was also equipped with a side-arm light probe for observing chemiluminescence produced during CHHP decomposition. Light produced by chemiluminescence passed through a flexible light guide to a photomultiplier (PM). Current output from the photomultiplier (typically 0.1–100 nA) was converted to a voltage by an electrometer amplifier with good linearity and low noise characteristics. Voltages representing temperature (T) and chemiluminescent light intensity (I) were routed to an analog/digital converter and the resulting output stored on disks and magnetic tapes in a computer system.

COMPARATIVE EXAMPLES A–G; EXAMPLES 1–5

Except for changes in amounts of catalyst added to the reactor, reaction temperatures, and amounts of added air, the experiments illustrated by Comparative Examples A–F and Examples 1–5 were performed substantially similarly, according to the following procedure:

The pulse reactor previously described was charged with 25 ml cyclohexane and 0.1 ml steam-distilled K and A (SDKA). SDKA is a plant process mixture of K, A and other compounds obtained from steam distillation of CHHP decomposition reactor product, containing about 1% residual peroxides and about 15±2% water. SDKA composition can vary depending upon such factors as plant process parameters and type of catalyst employed. A GC analysis of a representative SDKA sample is set forth in Table 1, below:

TABLE 1

| GC ANALYSIS OF SDKA SAMPLE | |
|---|---|
| Constituent | Approximate % (W/W) |
| Water | 17 |
| A | 56 |
| K | 24 |
| CHHP | 0.2 |
| Dicyclohexyl ether | 0.3 |
| Dicyclohexyl peroxide | 0.5 |

A 5% $Co_3O_4/SiO_2$ catalyst composition was added to the foregoing cyclohexane/SDKA mixture, and then the reactor was sealed and purged of air with gaseous nitrogen. A heating tape attached to the reactor head was heated to about 130° to prevent liquid accumulation in the top of the reactor. After about twenty minutes, the reactor was placed in a fluidized sand bath heated to an appropriate temperature to give the internal liquid temperatures indicated in Table 2, below. At this point, thermal and light monitoring sensors were connected to the computer and baseline measurements taken for about five minutes. Next, 2.25 ml of concentrated water-washed air oxidizer tails (W/W A/O tails) containing CHHP was injected and allowed to react in the stirred reactor for about twenty minutes. The W/W A/O tails samples were obtained from a plant cyclohexane air oxidate sample (A/O tails) which was water-washed, concentrated, and then diluted with cyclohexane to give about 1% CHHP. At the end of the reaction period, the reactor was quickly cooled in an ambient temperature water bath.

After cooling to ambient temperature, the reactor was opened and its contents analyzed by GC to determine relative concentrations of cyclohexanone (K), cyclohexanol (A), cyclohexyl hydroperoxide (CHHP) and dicyclohexyl peroxide (DCHP). Approximate concentrations of oxidized carbon material (OM$_C$) in each product sample were determined by extraction of known amounts of each product solution with 70% $H_2SO_4$. Carbon concentrations in each extract were determined with an Astro Model 1850 total organic carbon analyzer.

In the experiments illustrated by Comparative Examples A–E and G, no air or molecular oxygen was added to the reaction mixtures. In the experiment represented by Comparative Example F, 10 ml/min $N_2$ was introduced into the reactor. In Examples 1–5, air was added at the rates indicated in Table 2, below. The rates of addition of air or $N_2$ indicated in Table 2 were regulated with a Brooks Instruments model 5874 gas mass flow controller in conjunction with a back pressure regulator.

The experimental results of Comparative Examples A–G, and Examples 1–5, are set forth in Table 2, below:

In the case of the starting solution (sample), the ratio 1.30 is a calculated value representing 100% theoretical conversion of CHHP to K and A.

GC analyses for residual CHHP in each of the product solutions of the Comparative Examples and Examples show that at least 95% (GC area percent) of the CHHP was decomposed in each experiment. Comparison of the results of Examples 2–4, in which air was added to the reaction mixture, with the results of Comparative Examples A–C, in which no air was added, shows that addition of air at 115° in the presence of $Co_3O_4/SiO_2$ increases the average useful product/$OM_c$ ratio from 1.21 to 1.27.

This comparison also indicates that adding air increases product K/A ratios, on average, from 0.46 to

TABLE 2

Analysis of CHHP Decomposition Experiments

| A Example No. | B Cat. Amt. (g) | C T: °C. | D Air added: (ml/min; psi) | E A | F K | G CHHP | H DCHP | I $OM_C$ (ppmC) | J K/A Ratio | K Useful Product/ $OM_C$ Ratio |
|---|---|---|---|---|---|---|---|---|---|---|
| Sample | — | — | — | 1.363 | 0.642 | 0.988 | 0.023 | 2337 | 0.47 | 1.30 |
| A | 0.130 | 115 | — | 1.790 | 0.837 | 0.054 | 0.044 | 2333 | 0.47 | 1.19 |
| B | 0.260 | 115 | — | 2.166 | 1.000 | 0.033 | 0.049 | 2689 | 0.46 | 1.23 |
| C | 0.250 | 115 | — | 2.154 | 0.977 | 0.012 | 0.063 | 2720 | 0.45 | 1.20 |
| D | 0.250 | 122 | — | 2.105 | 0.956 | 0.010 | 0.069 | 2690 | 0.45 | 1.19 |
| E | 0.250 | 132 | — | 2.110 | 0.969 | — | 0.061 | 2650 | 0.46 | 1.21 |
| F | 0.250 | 114 | 10;160* | 2.213 | 0.980 | 0.025 | 0.061 | 2700 | 0.44 | 1.24 |
| 1 | 0.250 | 120 | 20;100 | 2.553 | 1.335 | 0.039 | 0.043 | 3168 | 0.52 | 1.26 |
| 2 | 0.500 | 113 | 10;100 | 2.389 | 1.207 | — | 0.062 | 3004 | 0.50 | 1.24 |
| 3 | 0.210 | 115 | 10;160 | 2.412 | 1.257 | 0.051 | 0.051 | 2950 | 0.52 | 1.30 |
| 4 | 0.250 | 113 | 10;165 | 2.401 | 1.164 | 0.038 | 0.052 | 2920 | 0.48 | 1.27 |
| 5 | 0.250 | 113 | 15;165 | 2.388 | 1.292 | 0.044 | 0.034 | 2970 | 0.54 | 1.28 |
| G | — | 165 | — | 2.402 | 0.927 | — | — | 2997 | 0.39 | 1.12 |

*In Comparative Example F, nitrogen, rather than air, was injected into the experimental reactor.

DISCUSSION

The experimental results of Comparative Examples A–G, and Examples 1–5 are summarized in Columns A–K of Table 2, above. The row marked "Sample" in column A contains the results of an analysis of an unreacted sample mixture submitted for GC and carbon analysis. Column B lists the amount, in grams, of a 5% $Co_3O_4/SiO_2$ catalyst composition, ground to a fine powder, which was added to the reactor in each experiment. In the experiment represented by Comparative Example G, a sufficient amount of a Co(II)ethylhexanoate solution was added to provide a final cobalt concentration of about 1 ppm.

Column C lists the temperatures at which experimental reactions were conducted, and column D sets forth the rates of addition of air or nitrogen to the various reaction mixtures. Columns E through H list relative concentrations of K, A, CHHP, and DCHP in the respective product mixtures, as determined by GC. Column I lists the $OM_C$ values determined as previously described. Parts per million (ppm) carbon were determined by comparison to reference solutions of known amounts of K and A in the range of 2500 to 3000 ppm carbon by weight in cyclohexane. Column J lists K/A ratios of the resulting product mixtures, and Column K sets forth ratios of the relative amounts of useful product compounds to total oxidized carbon material, calculated as follows:

$$\frac{A + K + CHHP + 2DCHP}{OM_c} \times 10^3$$

0.50. Comparative Example G shows that decomposition of CHHP under conditions commonly used commercially (165°; Co(oct)$_2$ catalyst) results in a lower useful product/$OM_c$ ratio and a lower K/A ratio than that obtainable with the catalyst composition of the invention at 115° in the presence of added air (Examples 2–4).

DISCUSSION OF COMPARATIVE EXAMPLES H, I AND J AND EXAMPLE 6

Comparative Examples H, I and J and Example 6, which are illustrated by FIGS. 1–8, were performed using the pulse reactor previously described, under similar experimental conditions. The reaction temperatures employed ranged from about 115° to about 130°.

CHHP decomposition produces chemiluminescence, and the intensity of light emitted at any time is a direct measure of the rate of decomposition. In addition, CHHP decomposition is an exothermic reaction, and the progress of a given reaction can be monitored by observing the temperature of the reaction mixture. FIGS. 1–8 illustrate the chemiluminescence and temperature observations corresponding to Example 6 and Comparative Examples H, I and J.

Comparative Example H (FIGS. 1 and 2) was performed in the following manner. First, the reactor was charged with 25 ml cyclohexane and 0.5 g powdered 5% $Co_3O_4/SiO_2$ catalyst. The reactor was sealed, purged of air, and pressurized to 1034 kPa (150 psi) with $N_2$. The temperature of the reactor contents was permitted to equilibrate for about five minutes and then six sequential 0.5 ml injections of 50% CHHP in W/W A/O tails were made at intervals of about two minutes.

Figure 2:
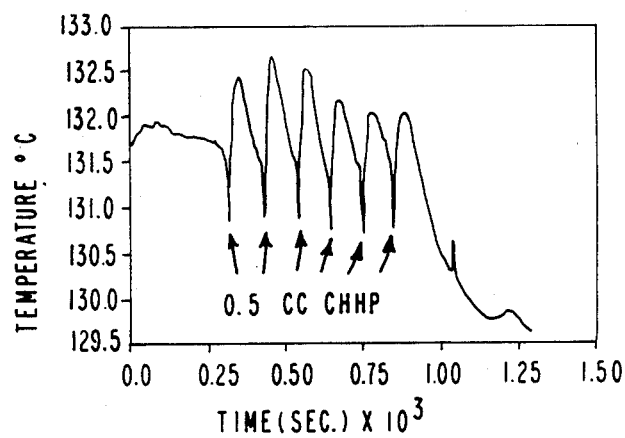

The light and heat traces of FIGS. 1 and 2 show no significant loss of CHHP decomposition catalyst activity during the six injections of CHHP.

Figure 3:
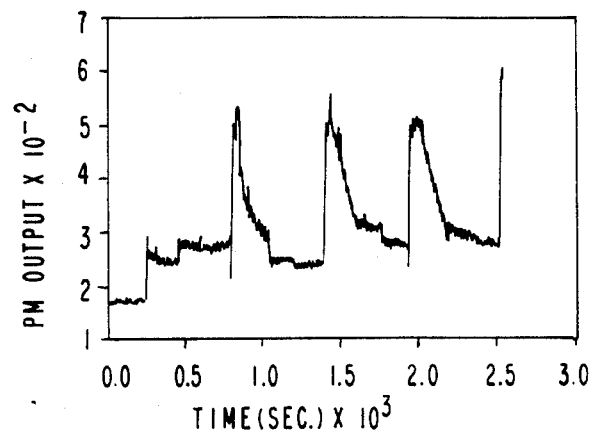
Figure 4:
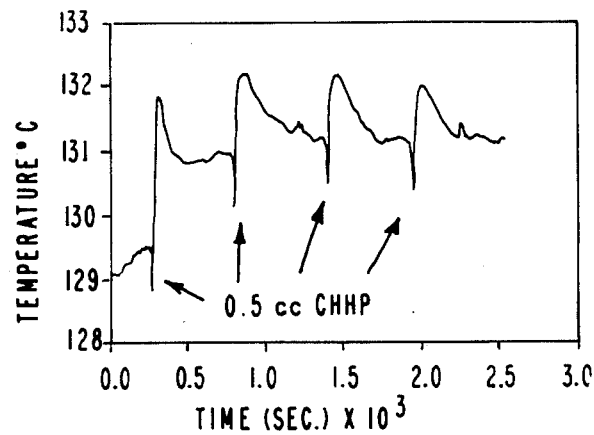
Figure 5:
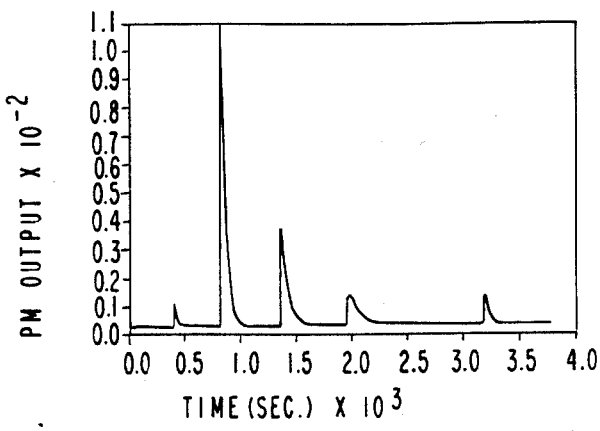
Figure 6:
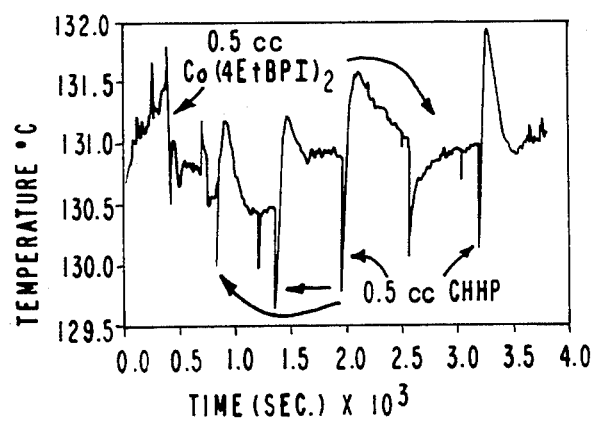

Example 6, illustrated by the thermographic and chemiluminescent tracings of FIGS. 3 and 4, was performed in substantially similar fashion to Comparative Example H, except that air at 150 psi was used and only four injections of CHHP were made. The light and heat traces of FIGS. 3 and 4 demonstrate that catalyst activity for CHHP decomposition remained relatively constant throughout the four CHHP injections, in the presence of added air.

Figure 7:
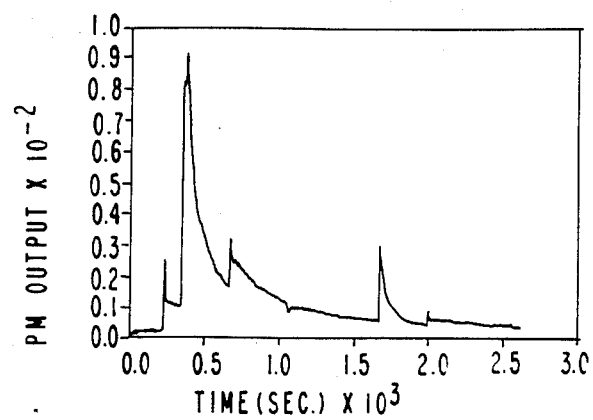
Figure 8:
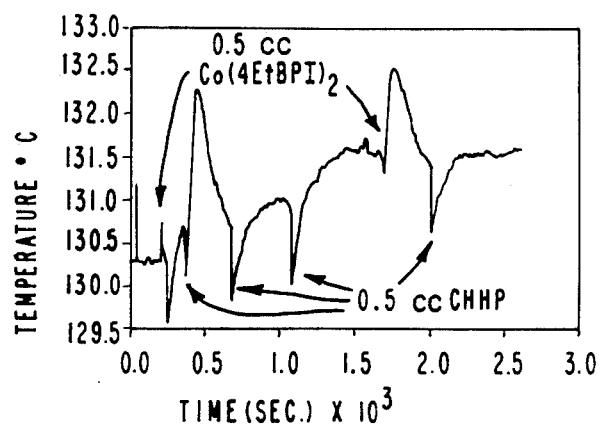

Comparative Examples I and J, illustrated by FIGS. 5-8, were performed using a soluble Co(4EtBPI)$_2$ catalyst CHHP decomposition was accomplished under 150 psi N$_2$ and air, respectively. Comparison of the light (FIGS. 5 and 7) and heat traces (FIGS. 6 and 8) indicates that CHHP decomposition activity of a soluble Co(4EtBPI)$_2$ catalyst is reduced by the addition of air. The catalytic activity of the Co(4EtBPI)$_2$ catalyst of Comparative Example J was almost completely quenched by air by the time the second CHHP injection was made (FIGS. 7 and 8).

I claim:

1. In a process for producing a mixture containing cyclohexanol and cyclohexanone, wherein cyclohexyl hydroperoxide is decomposed in the presence of cyclohexane to provide a mixture containing cyclohexanol and cyclohexanone, the improvement comprising contacting a reaction mixture comprising cyclohexane and from about 0.1 to about 10 percent by weight cyclohexyl hydroperoxide with a catalytic amount of a heterogeneous catalyst consisting essentially of MnO$_2$ or FeO$_3$O$_4$ applied to a catalyst support selected from the group consisting of SiO$_2$, porous glass, Al$_2$O$_3$, TiO$_2$, ZrO$_4$, and carbon, said catalyst support characterized by a surface area to weight ratio of at least 1 m$^2$/g, at a temperature from about 80° C. to about 130° C., in the presence of from about 0.5 to about 4 moles of molecular oxygen per mole of cyclohexyl hydroperoxide to be decomposed.

2. A process according to claim 1 wherein the temperature is from about 110° C. to about 130° C., and reaction pressure is from about 69 kPa to about 2760 kPa.

3. A process according to claim 2 wherein the reaction pressure is from about 276 kPa to about 2760 kPa.

4. A process according to claim 3 wherein the reaction mixture contains from about 0.5 to about 3 percent by weight cyclohexyl hydroperoxide.

5. A process according to claim 4 wherein the heterogeneous catalyst is Co$_3$O$_4$ applied to SiO$_2$.

6. A process according to claim 5 wherein the heterogeneous catalyst comprises from about 3 to 10 weight percent Co$_3$O$_4$.

7. A process according to claim 5 wherein the heterogeneous catalyst is Co$_3$O$_4$ applied to porous glass.

8. A process according to claim 7 wherein the heterogeneous catalyst comprises from about 0.5 to 10 weight percent Co$_3$O$_4$.

* * * * *